United States Patent
Schiendzielorz (10) Patent No.: US 10,166,325 B2
(45) Date of Patent: Jan. 1, 2019

(54) PACKAGING FOR MEDICAL DEVICE AND MEDICAMENT

(71) Applicant: Sanofi, Paris (FR)

(72) Inventor: Eva Schiendzielorz, Frankfurt am Main (DE)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 15/508,587

(22) PCT Filed: Sep. 11, 2015

(86) PCT No.: PCT/EP2015/070864
§ 371 (c)(1),
(2) Date: Mar. 3, 2017

(87) PCT Pub. No.: WO2016/041868
PCT Pub. Date: Mar. 24, 2016

(65) Prior Publication Data
US 2017/0252507 A1  Sep. 7, 2017

(30) Foreign Application Priority Data
Sep. 15, 2014  (EP) .................................... 14306416

(51) Int. Cl.
*A61M 5/00* (2006.01)
*B65D 81/20* (2006.01)
(Continued)

(52) U.S. Cl.
CPC .............. *A61M 5/002* (2013.01); *A61M 5/24* (2013.01); *B65D 77/20* (2013.01); *B65D 77/22* (2013.01);
(Continued)

(58) Field of Classification Search
CPC .. A61J 1/03; A61J 19/02; A61M 5/00; A61M 5/002; A61M 5/24; A61M 2005/2414;
(Continued)

(56) References Cited

U.S. PATENT DOCUMENTS 4,243,140 A * 1/1981 Thrun .............. A61B 17/06161
206/460
8,282,046 B2 10/2012 Harding et al.
(Continued)

FOREIGN PATENT DOCUMENTS

EP  2 502 643  9/2012

OTHER PUBLICATIONS

Extended European Search Report in European Application No. 14306416.0, dated Mar. 16, 2015, 5 pages.
(Continued)

*Primary Examiner* — Bryon Gehman
(74) *Attorney, Agent, or Firm* — Fish & Richardson P.C.

(57) ABSTRACT

A packaging for a medical device and medicament comprising a packaging body having a first region and a second region. A medicament delivery device comprises a delivery mechanism for administering medicament to a patient. The medicament delivery device is received in the first region and a medicament container is received in the second region. The medicament delivery device includes a chamber configured to receive the medicament container. The packaging body includes a hinge between the first and second regions such that the first and second regions are pivotable about the hinge from a storage position in which the first and second regions are spaced apart to a loading position in which the first region lies adjacent the second region. The chamber and medicament container are equidistantly spaced from the
(Continued)

hinge such that the medicament container is loaded into the chamber when the first and second regions are pivoted into the loading position.

22 Claims, 5 Drawing Sheets

(51) Int. Cl.
*A61M 5/24* (2006.01)
*B65D 77/20* (2006.01)
*B65D 77/22* (2006.01)

(52) U.S. Cl.
CPC ..... *B65D 81/2015* (2013.01); *B65D 81/2076* (2013.01); *A61M 2005/247* (2013.01); *A61M 2005/2414* (2013.01); *A61M 2005/2496* (2013.01)

(58) Field of Classification Search
CPC .... A61M 2005/247; A61M 2005/2496; B65D 77/20; B65D 77/22; B65D 81/20; B65D 81/2015; B65D 81/2016; B65D 81/2076
USPC ............... 206/363–365, 460, 570–572; 220/4.22–4.23
See application file for complete search history.

(56) References Cited

U.S. PATENT DOCUMENTS

| | | | |
|---|---|---|---|
| 8,517,989 B2* | 8/2013 | Duncan | A61M 5/002 604/143 |
| 2007/0156099 A1* | 7/2007 | Fowler | A61M 5/003 604/189 |
| 2014/0262884 A1* | 9/2014 | Priebe | A61J 1/03 206/365 |
| 2015/0014210 A1* | 1/2015 | Priebe | A61J 1/03 206/571 |

OTHER PUBLICATIONS

International Preliminary Report on Patentability in International Application No. PCT/EP2015/070864, dated Mar. 21, 2017, 6 pages.

International Search Report and Written Opinion in International Application No. PCT/EP2015/070864, dated Dec. 16, 2015, 9 pages.

* cited by examiner

PACKAGING FOR MEDICAL DEVICE AND MEDICAMENT

CROSS-REFERENCE TO RELATED APPLICATIONS

This application is a U.S. national stage application under 35 USC § 371 of International Application No. PCT/EP2015/070864, filed on Sep. 11, 2015, which claims priority to European Patent Application No. 14306416.0 filed on Sep. 15, 2014, the entire contents of which are incorporated herein by reference.

TECHNICAL FIELD

The present disclosure relates to packaging for a medical device and associated medicament.

BACKGROUND

A variety of diseases exist that require regular treatment by injection of a medicament. Injection devices known in the art include infusion and patch pumps for delivering injections of medicament. Another type of injection device that is gaining traction is a bolus injector device. Biological medicaments are being increasingly developed which comprise higher viscosity injectable liquids and which are to be administered in larger volumes than traditional liquid medicaments. Some bolus injectors are intended to be used with relatively large volumes of medicament, typically at least 1 ml and maybe a few ml. Injection of such large volumes of medicament can take some minutes or even hours. Such high capacity bolus injectors can be called large volume devices (LVDs) and may comprise a pre-filled disposable medicament delivery device or, alternatively, a disposable medicament delivery device into which a patient or medical personnel must insert a medicament cartridge prior to use. To use an injection device such, as an LVD, it is first supported on a suitable injection site of a patient and, once installed, injection is initiated by the patient or another person (a user).

Particularly in the case of patient-operated devices which require insertion of a medicament cartridge prior to use, the drug delivery process from start to finish can be a complicated multi-step process. Steps can include gathering all of the device components, removal of each from their respective packaging, assembly of the components to ready the device for medicament administration before the actual process of injecting the medicament can even begin. Such devices may also require insertion of a battery, a needle assembly and/or other component(s) prior to use of the device. Such processes are therefore complicated for the patient to remember, intrusive upon his or her daily schedule, and increase the risk that the patient may not correctly perform the medicament administration. In addition, a patient may have limited dexterity or other ailments making assembly of the device components difficult.

SUMMARY

Certain embodiments provide a packaging for a medical device and medicament comprising a packaging body having first and second regions, a medicament delivery device received in the first region, and a medicament container received in the second region, the medicament delivery device including a chamber configured to receive the medicament container, the packaging body including a hinge between the first and second regions such that the first and second regions are pivotable about the hinge between a storage position in which the first and second regions are spaced apart, to a loading position in which the first region lies adjacent the second region, the chamber and medicament container being equidistantly spaced from the hinge such that the medicament container is loaded into the chamber when the first and second regions are pivoted into the loading position. The packaging may therefore allow a patient to load the medicament container into the chamber without the need to handle the container or the medicament delivery device, and therefore helps avoid the risk of contamination of the medicament delivery device or medicament container. This also may help to avoid incorrect use of the device, for example by helping avoid incorrect loading of the medicament container into the chamber.

The first and second regions may each comprise a recess in the packaging body. Such recess(es) may advantageously securely retain the medical apparatus components in place in the packaging body.

The packaging body may be a unitary component and the hinge may be a living hinge formed integrally with the packaging body. Forming the packaging body as a unitary component, that is as a single component, may advantageously enable a cost effective and/or simpler and/or quick method of packaging manufacture. The body may be made of plastic, or cardboard, or a combination of materials. The living hinge may be one or more lines of weakening in the material of the body.

In an alternative embodiment, the body may be made of separate components connected together. The first and second regions may comprise separate components connected together. The separate components may be connected by a further component comprising the hinge.

The medicament delivery device may include a needle through which medicament is received from the medicament container in use, and the medicament container may comprise a pierceable region to be pierced by the needle of the medicament delivery device. Such an arrangement may comprise a convenient method of medicament access and transfer from the medicament container to the medicament delivery device.

The medicament delivery device may be configured to automatically pierce the pierceable region of the medicament container when the first and second regions of the packaging body are pivoted into the loading position and the medicament container is loaded into the chamber. This may provide an efficient medicament container loading process, reduces the number of preparation steps required to be performed by a patient and improves the usability of the overall apparatus. This may also help avoid incorrect use of the medicament delivery device by a patient.

The medicament container may comprise a cartridge and the pierceable region may comprise a seal over an opening in the cartridge.

The medicament container may be adhered to the second region of the packaging body by a non-permanent adhesive. This may advantageously retain the medicament container in place during packaging folding and/or medicament delivery device loading movement.

The medicament delivery device may include a holding mechanism for retaining the medicament container within the chamber and the force required to remove the medicament container from the holding mechanism may be greater than the force with which the non-permanent adhesive secures the medicament container to the second region of the packaging body. This may advantageously ensure the medicament container is retained in the medicament delivery device chamber once medicament container is loaded and the second region is folded back away from the first region.

The packaging may further comprise a cover secured to the packaging body and covering at least one of the first and second regions to define a sealed interior space within the packaging.

The packaging may comprise a cover secured to the packaging body and covering the first and second regions to define a sealed interior space within the packaging. Alternatively, the packaging may further comprise a first cover secured to the packaging body and covering the first region to define a first sealed interior space within the packaging, and a second cover secured to the packaging body and covering the second region to define a second sealed interior space within the packaging. The cover(s) may advantageously prevent ingress of ambient contaminants to medicament delivery device and/or medicament container.

Each sealed interior space may comprise an inert atmosphere, or may comprise an at least partial vacuum. This may advantageously further help prevent contamination of the medicament delivery device and/or medicament container.

The medicament container may contain a medicament.

Certain embodiments also provide a method of use of a packaging for a medical device and medicament comprising a packaging body having first and second regions a medicament delivery device received in the first region and a medicament container received in the second region, the medicament delivery device including a chamber configured to receive the medicament container, the packaging body including a hinge between the first and second regions, the first and second regions being pivotable about the hinge between a storage position to a loading position, the chamber and medicament container being equidistantly spaced from the hinge, the method comprising pivoting the first and second regions about the hinge from the storage position in which the first and second regions are spaced apart to the loading position in which the first region lies adjacent the second region, and causing the medicament container to be loaded into the chamber by the first and second regions being pivoted into the loading position.

Certain embodiments also provide a medical apparatus comprising a packaging for a medical device and medicament comprising a packaging body having first and second regions, a medicament delivery device received in the first region and a medicament container received in the second region, a detachable cover secured to the packaging body and covering at least one of the first and second regions to define at least one sealed interior space within the packaging containing the medicament delivery device and/or the medicament container, the medicament deliver device including a chamber configured to receive the medicament container and an injection mechanism for injecting medicament from the medicament container into the patient's body, the packaging body including a hinge between the first and second regions such that, upon removal of the at least one cover the first and second regions are pivotable about the hinge between a storage position in which the first and second regions are spaced apart, to a loading position in which the first region lies adjacent the second region, the chamber and medicament container being equidistantly spaced from the hinge such that the medicament container is loaded into the chamber when the first and second regions are pivoted into the loading position.

BRIEF DESCRIPTION OF THE DRAWINGS

Embodiments will now be described, by way of example only, with reference to the accompanying drawings, in which.

DETAILED DESCRIPTION

FIGS. 1 to 5 show a medicament packaging 10 according to a first embodiment which comprises a packaging body 11 (hereafter "body 11") having a first region 12 that comprises a recess 12a in which a medicament delivery device 13 is received, such as a bolus injector device (hereafter referred to as "device 13"). The body 11 includes a second region 14 which comprises a recess 14a in which a medicament container 15 is received. The body 11 includes a hinge 16 extending across the body 11 between the first and second regions 12, 14 and about which the first and second regions 12, 14 of the body 11 can pivot relative to each other.

Figure 1:
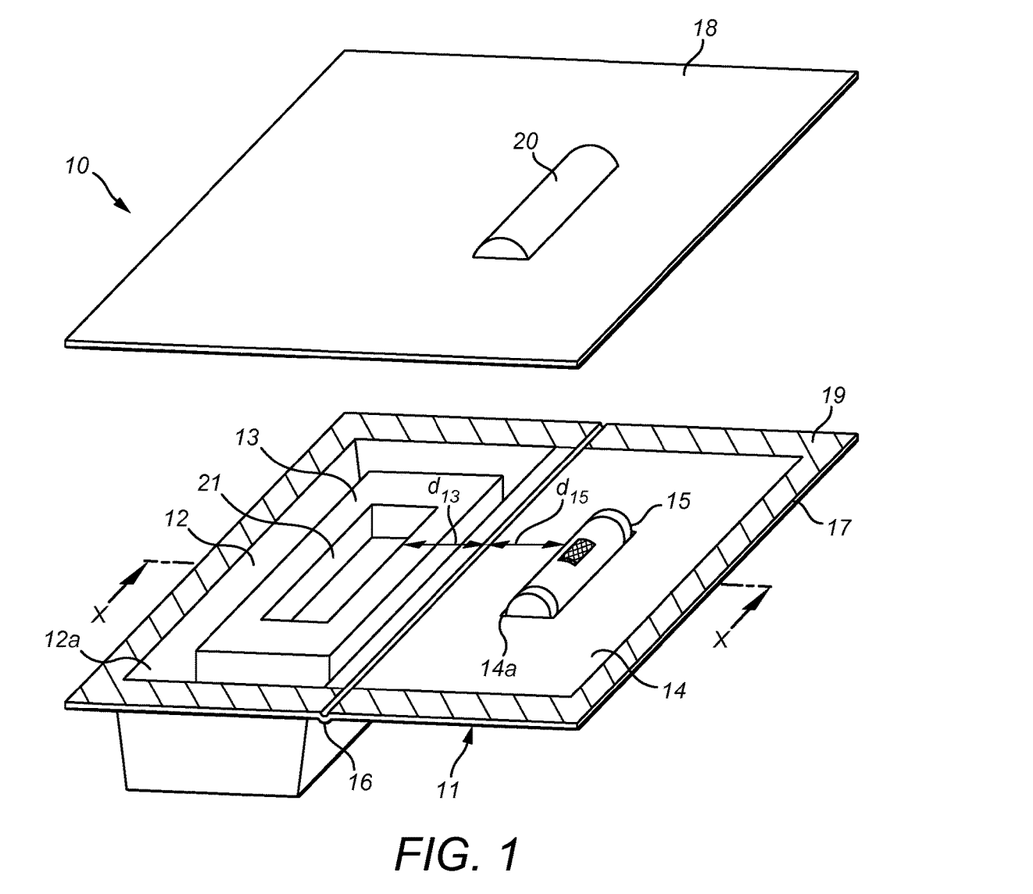
FIG. 1 shows a perspective view of a packaging of a first embodiment including a medicament delivery device and a medicament container, with a cover removed and in an unused position.
Figure 2:
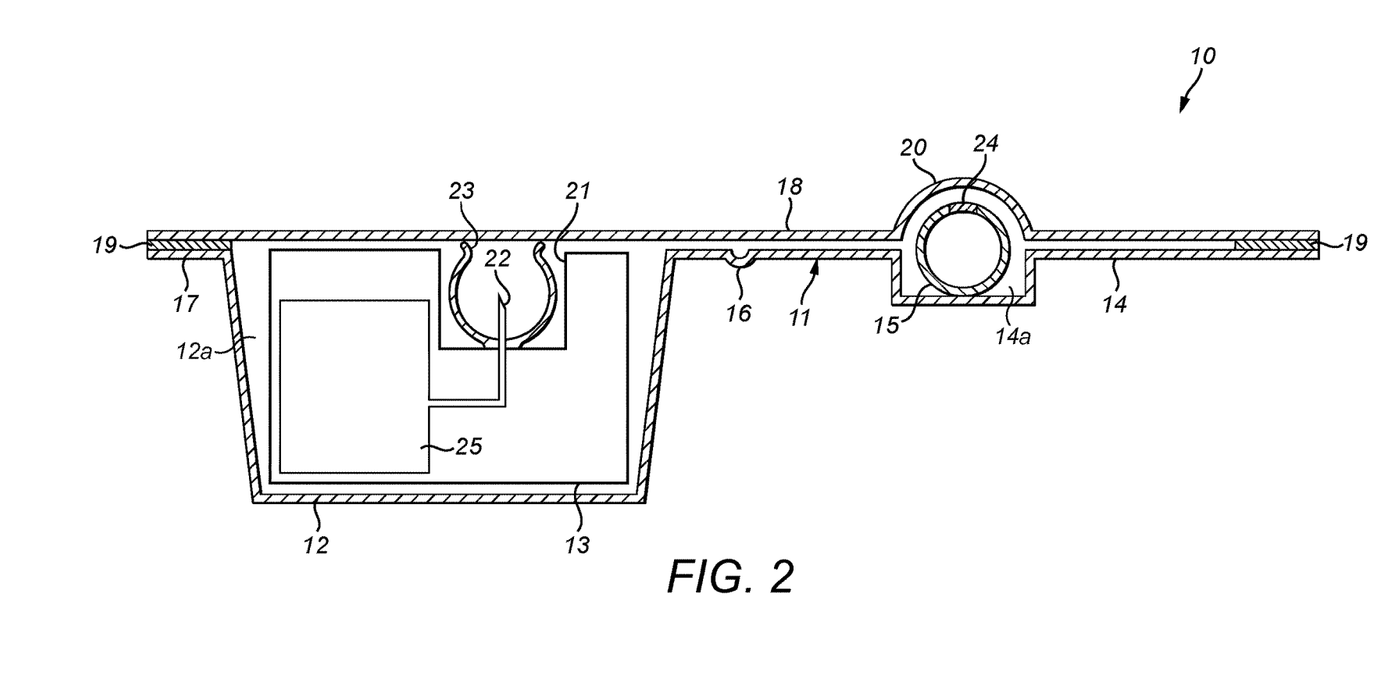
FIG. 2 shows a cross-section of the packaging along the line X-X shown in FIG. 1, but with the cover secured on the body of the packaging.

The body 11 includes a flange 17 extending around the outer periphery of the body. A cover 18 is secured to the body 11 by adhesive 19 around the flange 17. The cover 18 includes a raised area 20 to accommodate part of the medicament container 15 that projects from the second region 14 of the body 11.

Figure 3:
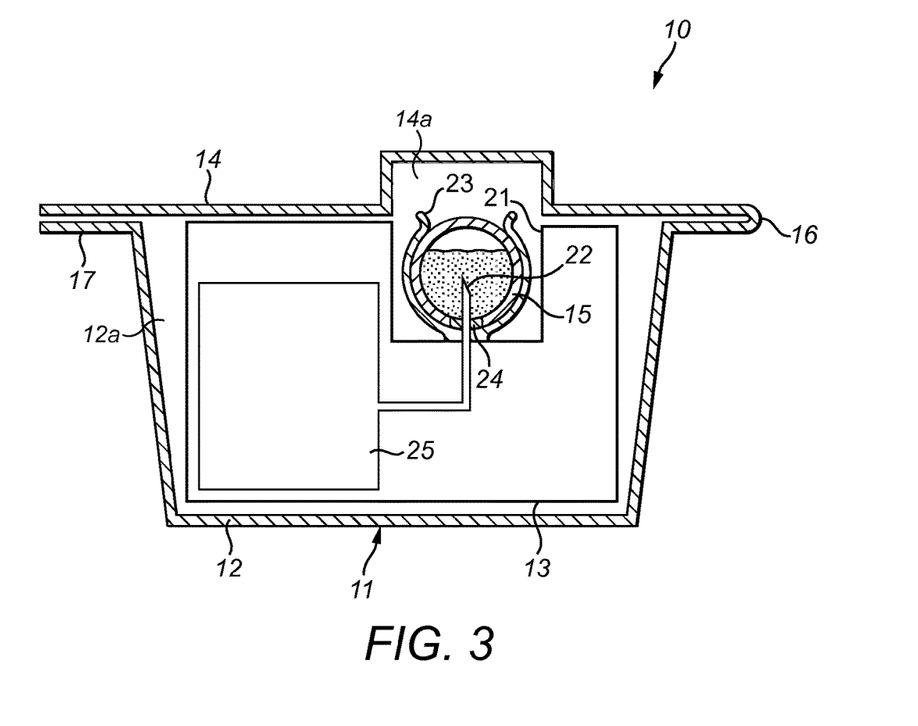
FIG. 3 shows a cross-section of the packaging similar to the view of FIG. 2 but with the cover removed and the packaging folded into a loading position.
Figure 4:
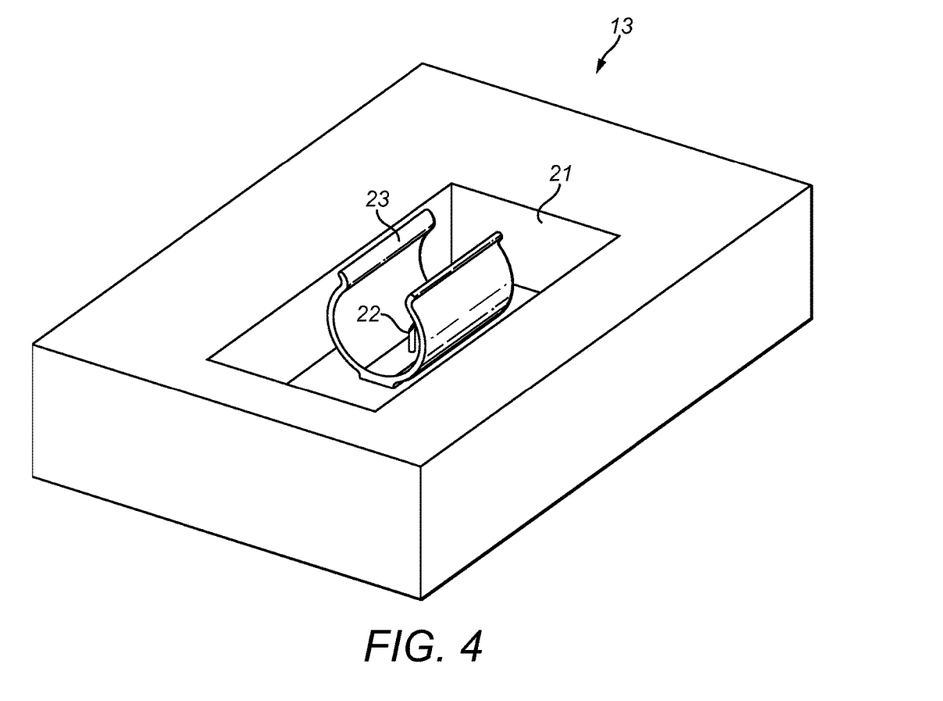
FIG. 4 shows a perspective view of the medicament delivery device shown in FIGS. 1 and 2.

The device 13 is shown schematically in FIGS. 2 to 4, and a number of the functional components are omitted for the sake of clarity and brevity. However, the device 13 includes a chamber 21 configured to receive a medicament container 15. The device 13 also includes a needle 22 within the chamber 21 configured to pierce a portion of a medicament container 15 when inserted into the chamber 21. This allows the medicament within the medicament container 15 to transfer to a delivery mechanism (indicated generally at 25) of the device 13 to be administered to a patient. A retaining clip 23 is provided within the chamber 21 to engage with and secure the medicament container 15 in place.

Figure 5:
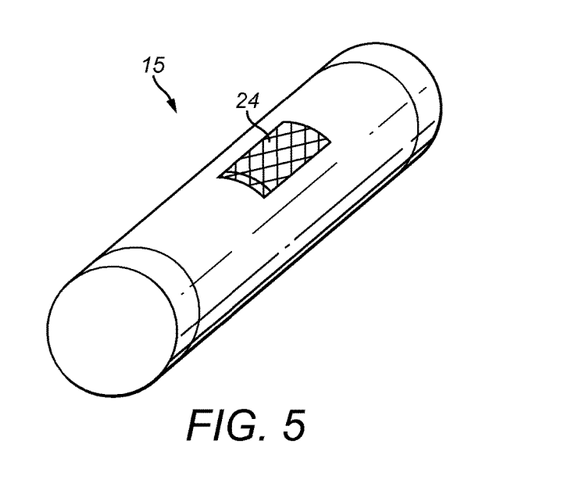
FIG. 5 shows a perspective view of the medicament container shown in FIGS. 1 and 2.

The medicament container 15 is shown in FIG. 5 and comprises a generally cylindrical cartridge of liquid medicament and includes a pierceable seal 24 on a side face of the cartridge. It can be seen from FIGS. 1 and 2 that when the medicament container 15 is received in the second region 14 of the body 11, the pierceable seal 24 faces uppermost, that is, away from the body 11. The medicament container 15 is temporarily adhered in place on the second region 14 of the body 11 by a non-permanent adhesive (not shown).

When the cover 18 is secured on the body 11 by the adhesive 19 around the flange 17, a sealed space is defined between the body 11 and the cover 18 which contains the device 13 and the medicament container 15. This sealed space is sterile and may be filled with an inert gas, or may be formed with a vacuum or at least a partial vacuum. The sealed space may include a sterilizing agent to maintain the sterility over a period of time so that the interior space remains sterile during extended periods of storage before use.

Use of the packaging 10 will be described in terms of use by a patient in self-administration of a medicament. However, it will be appreciated that the packaging 10 is not limited to such use and the packaging may alternatively be used by a third party, for example by medical personnel. In use, a patient takes the packaging 10 and removes the cover 18 exposing the device 13 and medicament container 15 within the body 11. The user then pivots the second region 14 of the body about the hinge 16 relative to the first region 12, from the initial storage position into the loading position shown in FIG. 3. Since the medicament container 15 is adhered within the recess 14a of the second region 14, it remains fixed in place during this pivoting action. The configuration of the packaging 10 is such that when the packaging 10 is folded into the loading position, the medicament container 15 is inserted into the chamber 21 of the device 13 and is held in place by the retaining clip 23. Once inserted into the chamber 21, the needle 22 pierces the pierceable seal 24 and the device 13 is then able to draw the medicament from within the medicament container 15. The body 11 may be made from a deformable material so that a user may press the outside of the body 11 when the packaging 10 is in the loading position and deflect the body 11 to push the medicament container 15 further towards the device 13 to ensure the medicament container 15 is fully received within the chamber 21 of the device 13.

The second region 14 of the body 11 is subsequently pivoted away from the first region 12 to allow the patient to access and remove the device 13 from the packaging 10 and to administer the medicament. As the second region 14 is pivoted away from the first region 12, the retaining clip 23 holds the medicament container 15 in place within the chamber 21. The retaining clip 23 is configured such that the force that is required to release the medicament container 15 from the retaining clip 23 is greater than the force required to overcome the non-permanent adhesive holding the medicament container 15 within the recess 14a of the second region 14. Therefore, as the second region 14 is pivoted away from the first region 12, the medicament container 15 detaches from the second region 14 and remains secured within the device 13.

It will be appreciated from the above that packaging 10 is configured such that the medicament container 15 and the chamber 21 of the device 13 are spaced equally from the hinge 16 on opposite sides of the hinge 16 to enable the medicament container 15 to be folded into position in the chamber 21 as described. This is shown by distance $d_{13}$ being equal to distance $d_{15}$ in FIG. 1. This advantageous arrangement of the packaging 10 enables a patient to easily set the device 13 up for medicament delivery with minimum number of steps and little chance of error. Also, since the components of the device 13 are assembled within a sterile packaging without the need for a patient to handle the components or set them out before assembly, it avoids the need for a user to prepare a sterile surface upon which to place the medicament delivery device components. These all may contribute to making the medicament administration process quick and easy, and to minimize impact on the patient's lifestyle and daily routine. This aspect of the packaging and medicament delivery apparatus is psychologically beneficial for a patient so that the treatment of their illness causes little disruption to their daily routine and is simple to use.

Figure 6:
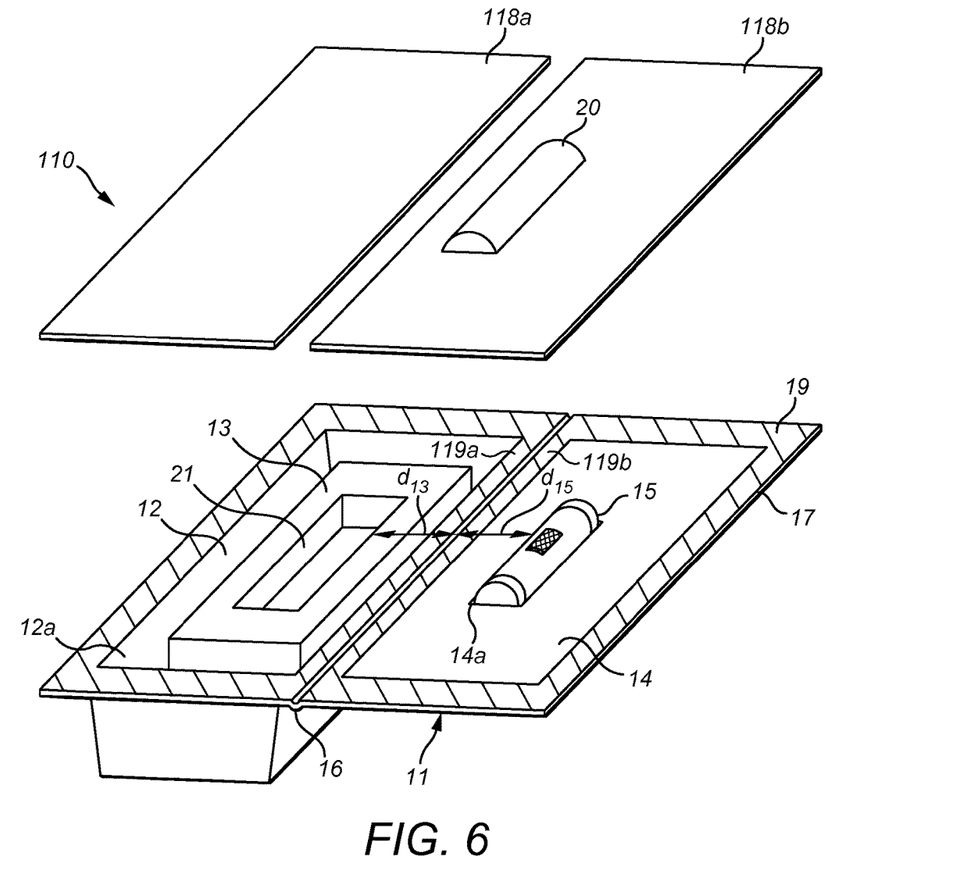
FIG. 6 shows a perspective view of a packaging of a second embodiment including a medicament delivery device and a medicament container, with separate covers removed and in an unused position.

FIG. 6 shows a medicament packaging 110 according to a second embodiment and is similar to the packaging 10 of the first embodiment shown in FIG. 1. Like features retain the same reference numerals and a detailed description of such features will not be repeated. A difference between the packaging 110 of the second embodiment over the packaging 10 of the first embodiment is that the packaging 110 of the second embodiment includes two separate covers 118a, 118b instead of one single cover 18. A first cover 118a is secured to the body 11 over the first region 12 by adhesive 19 around the flange 17. A second, separate cover 118b is secured to the body 11 over the second region 14 by adhesive 19 around the flange 17. The second cover 118b includes a raised area 20 to accommodate part of the medicament container 15 that projects from the second region 14 of the body 11.

The body includes additional lines of adhesive 119a, 119b one either side of the hinge 16, so that the first and second covers 118a, 118b are secured to the first and second regions 12, 14 respectively of the body 11 around their entire perimeter edge. In this way, when each cover 118a, 118b is secured on the body 11, a sealed space is defined between the body 11 and each cover 118a, 118b which respectively contains the device 13 and the medicament container 15. Each sealed space is sterile and may be filled with an inert gas, or may be formed with a vacuum or at least a partial vacuum. Each sealed space may include a sterilizing agent to maintain the sterility over a period of time so that the interior space remains sterile during extended periods of storage before use.

In use, a patient takes the packaging 110 and removes the first cover 118a, exposing the device 13, and removes the second cover 118b, exposing the medicament container 15. The user then pivots the second region 14 of the body about the hinge 16 relative to the first region 12 and from this point onwards, use of the packaging 110 of the second embodiment is the same as that of the first embodiment.

The packaging 110 of the second embodiment is advantageous as it may enable the packaging 110 to be assembled in separate process steps, and/or in separate locations. This may be advantageous because in assembly of the overall packaging 110, a manufacturer of the device 13 may be different to a manufacturer of the medicament container 15. Therefore, it may be desirable for the manufacturer of the device 13 to be provided with the body 11 and insert the device 13 into the first region 12 and seal the first region closed by applying the first cover 118a. The body 11 could then be transported to the manufacturer of the medicament container 15 who could insert a medicament container 15 into the second region 14 and seal the second region closed by applying the second cover 118b. The first and second regions could respectively be provided with the device 13 and medicament container 15 in sterile conditions and each region 12, 14 of the packaging could be sealed closed in a sterile environment in separate locations and/or in separate manufacturing steps.

The particular configuration of device 13 and medicament container 15 shown and described above are exemplary only and only to illustrate the inventive concept of the medicament packaging. It will be appreciated therefore that many other configurations of medicament delivery devices and medicament containers may be used with the packaging 10, 110, provided that the medicament delivery device is configured to receive a medicament container in the pivoting action of the packaging body 11 about the hinge 16, as described above. For example, alternative configurations of medicament container seal and piercing mechanism may be utilized, such as a piercing needle that is coupled to a mechanism to be automatically triggered to pierce a seal on an end of a medicament cartridge when the medicament cartridge is received in the medicament delivery device. Such a mechanism may comprise a lever actuated by the medicament cartridge being pushed into position within the medicament delivery device. Alternatively, the medicament container 15 may comprise a flexible pouch of medicament to be received in a corresponding chamber of a medicament delivery device which is configured to pierce the pouch when received in the chamber. Yet further, any alternative configuration of medicament reservoir to be received within a medicament delivery device may be used with the packaging 10, 110. The medicament container 15 may be of any suitable shape.

In yet a further alternative embodiment, the medicament delivery device may not necessarily automatically pierce the medicament container when the medicament container is pivoted into position to be received in the medicament delivery device. Instead, the medicament container may be secured in place and the patient may then manually operate the medicament delivery device to pierce the medicament container in a subsequent separate step.

In the exemplary embodiments of the packaging 10, 110 shown in FIGS. 1 to 6, the body 11 is formed of moulded plastic which has the advantage of cost-effective and quick manufacture. Also, the hinge 16 is formed as a living hinge in the moulded plastic body 11 as a line of reduced thickness in the body or as a recess or other deformation in the plastic body to facilitate pivoting of the first region 12 relative to the second region 14. Such living hinge may comprise a line or multiple lines of weakening in the material of the body 11. This may also include one or more score lines, perforations, or embossing of the material of the body 11. Again this is advantageous as being a cost-effective and easily manufactured configuration of packaging. The invention is not limited to this particular material and configuration and other materials and means of assembly of packaging are applicable. The body may, for example, alternatively be made from card, or a hybrid of materials, such as plastic laminated card. The hinge portion may be made from a different material to the rest of the body 11. For example, the hinge portion may be made from a more flexible material than the rest of the body 11. For example, the body may be made from stiff card and the hinge may be made from flexible plastic or rubber, or more flexible card.

The first and second regions 12, 14 of the body 11 may be made as separate components connected together at the hinge 11. This may be advantageous as the first region 12 containing the device 13 may be manufactured and assembled in a first process, and the second region containing the medicament container may be manufactured in a second, separate process. The two regions may subsequently be joined to make the packaging 10 in a third manufacturing process step. Such manufacturing process may advantageously be applicable to the second embodiment comprising first and second covers 118a, 118b. The hinge 16 may be provided as a flexible strip of material, or multiple flexible sections of material, joining the first and second regions 12, 14 together.

The hinge 16 may extend partially across the body 11. Multiple hinges 16 may lie generally along a similar axis. Moreover, tear-away sections (not shown) may be located at one or more ends of hinge 16 or form part of cover 18, 118a, 118b.

It will be appreciated that in the exemplary embodiments shown in FIGS. 1 to 6, the cover 18 is shown spaced from the body 11 in FIG. 1 and the thickness of the layer of adhesive 19 is shown exaggerated in FIG. 2, for ease and clarity of illustration.

The body 11 of the exemplary embodiments of packaging 10, 110 shown in FIGS. 1 to 6 comprise recesses 12a, 14a in the first and second regions 12, 14 which respectively receive the device 13 and medicament container 15. However, the invention is not intended to be limited to this configuration and the second region may not include any surface formations, and the medicament container 15 may be retained in place on the body 11, for example by a non-permanent adhesive.

The device 13 and/or the medicament container 15 may be retained on the body 11 of the packaging 10 by surface formations formed in the body 11. For example, the body 11 may be formed with projections which secure the device 13 and/or the medicament container 15 as a friction fit or snap-fit in place on the body 11. Such mechanical securing of the device 13 and/or the medicament container 15 may be in addition to, or instead of, use of a non-permanent adhesive.

A non-permanent adhesive may be used to secure the device 13 in the first region 12.

The device 13 may be retained in place within the recess 12a of the first region 12 with a greater force than the medicament container 15 is retained in place within the recess 14a of the second region 14. Furthermore, the medicament container 15 may be retained in the chamber 21 of the device 13 with a greater force than that which the medicament container 15 is held in place in the recess 14a of the second region 14. This is beneficial since once the body 11 is folded about the hinge 16 and the medicament container 15 is received in the chamber 21 of the device 13, unfolding the second region 14 away from the first region 12 results in the medicament container 15 detaching from the second region and remaining held within the chamber of the device 13, and also the device 13 remaining within the recess 12a of the first region 12. This helps provide a simple and intuitive set-up process for the patient.

A spring element (not shown) may be provided between the medicament container 15 and the second region 14 to assist detachment of the medicament container 15 from the second region 14.

The body 11 may include a spring or other biasing means to assist the folding of the first and second regions 12, 14 relative to each other into the loading position, preferably upon removal of the or each cover 18, 118a, 118b. This may help patients with limited dexterity use the packaging 10, 110.

Although the medicament container 15 shown in FIG. 5 comprises a pierceable seal 24, the container could alternatively include an alternative configuration of pierceable region. For example, a portion of the side wall of the medicament container may be made thinner than the rest of the container wall. The seal could also comprise a pierceable label or plug disposed over or in an aperture in the wall of the medicament container. Such a label or plug may be made of plastic, rubber or other suitable material. Furthermore, the device 13 and medicament container 15 may include alternative configuration of cooperating elements to allow medicament transfer from the medicament container to the device 13. For example, the device 13 and medicament container 15 may include cooperating valve elements which engage once the medicament container 15 is received in the chamber 21 of the device 13.

The packaging 10, 110 may be used with various types of medicament delivery devices and medicament containers, and may be usable with both liquid and gaseous medicament. For example, the medicament may comprise a gaseous inhalable medicament. Such a medicament may be provided in a pressurized medicament container such as a canister with a valve which may cooperate with a corresponding port in the medicament delivery device, or a pierceable region that may be pierced by a needle in the medicament delivery device.

The medicament container 15 may include a chamber cover member (not shown) when in the second region 14 of the body 11. Thereby, when the medicament container 15 is folded over and inserted into the chamber 21, the chamber cover member may be placed over the chamber 21 to close the chamber 21. The chamber cover member may include locking tabs to secure it in position over the chamber 21. Thereby, the medicament container 15 would be enclosed within the device 13.

The device 13 may include a sensor or other detector to detect when the medicament container 15 is correctly and fully received within the container 13. The device 13 may also include an alert means connected to the detector to inform the patient when the medicament container 15 is correctly inserted into the device 13. Such alert means may include a visible alert and/or an audible alert. For example an LED or other light, a buzzer or other sound-emitting means.

The cover 18 may serve to prevent the body 11 being folded into the loading position accidentally. For example, the cover 18 may need to be removed from the body 11 before the body can be folded about the hinge 16. The cover 18 may be formed from a stiff material that is difficult or impossible to fold, to prevent the body being folded before the cover 18 is removed. Also, the first and second covers 118a, 118b may be shaped to prevent the body 11 folding about the hinge 16 before one or both is removed. For example, one or both covers 118a, 118b may include projecting tabs, or interlocking elements (not shown), that may overlap the hinge 16 to prevent folding of the body 11 before one or both covers 118a, 118b is removed.

The device 13 may be configured to deliver the medicament subcutaneously, although it may instead be configured for intradermal injection, for instance using a microneedle, or for injection in some other manner.

The device 13 may be a bolus injector device of the type known as a Large Volume Device (LVD). An LVD injection device is configured to dispense a relatively large dose of medicament, in particular at least 1 ml and typically up to 2.5 ml, but possibly up to 10 ml.

The bolus injector device is configured to deliver a bolus of the respective medicament to bring a volume of the medicament into a patient's body within a predetermined time. The injection rate, however, may not be critical, i.e. tight control may not be necessary. However, there may be an upper (physiological) limit to the delivery rate in order to avoid damage to the tissue surrounding the delivery site. The time taken to deliver a bolus dose of medicament may be between a few minutes and many hours depending on a number of factors including the quantity (volume) of medicament, the viscosity of the medicament and the nature of the injection site at which the injection device is intended to be used.

From a user or Health Care Professional perspective, it is desirable for an injection device to be configured to minimally impact the patient's lifestyle and schedule, providing the patient with minimal reminder of his or her disease between the injections. The treatment schedule for therapies is usually intermittent, i.e. may be one injection per week, one injection every other week, or one per month. Therefore, the patient usually has no routine in dealing with his or her disease, and hence has minimal routine/experience in performing the required injections. Thus, configuration of the injection device and all associated apparatus and packaging to simplify its operation by patients is highly desirable.

The term "drug" or "medicament", as used herein, means a pharmaceutical formulation containing at least one pharmaceutically active compound. In some embodiments, the pharmaceutically active compound can have a molecular weight up to 1500 Da or may include a peptide, a protein, a polysaccharide, a vaccine, a DNA molecule, an RNA molecule, an enzyme, an antibody or a fragment thereof, a hormone or an oligonucleotide, or a mixture of the above-mentioned pharmaceutically active compound. Various types or subtypes of compounds are also contemplated. For example, RNA may include RNAi, siRNA, or miRNA. In other embodiments, the pharmaceutically active compound can be useful for the treatment or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis or rheumatoid arthritis. In some embodiments, the pharmaceutically active compound can comprise at least one peptide for the treatment or prophylaxis of diabetes mellitus or complications associated with diabetes mellitus such as diabetic retinopathy. The pharmaceutically active compound can also comprise at least one human insulin or a human insulin analogue or derivative, glucagon-like peptide (GLP-1) or an analogue or derivative thereof, or exendin-3 or exendin-4 or an analogue or derivative of exendin-3 or exendin-4 or a pharmaceutically acceptable salt or solvate thereof.

Insulin analogues can include, for example, Gly(A21), Arg(B31), Arg(B32) human insulin; Lys(B3), Glu(B29) human insulin; Lys(B28), Pro(B29) human insulin; Asp (B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivatives can include, for example, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyhepta-decanoyl) human insulin.

Exendin-4 can include, for example, Exendin-4(1-39).

Hormones can include, for example, hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, or Goserelin.

A polysaccharide can include, for example, a glucosaminoglycane, a hyaluronic acid, a heparin, a low molecular weight heparin or an ultra low molecular weight heparin or a derivative thereof, or a sulphated, e.g. a polysulphated form of the above-mentioned polysaccharides, and/or a pharmaceutically acceptable salt thereof. An example of a pharmaceutically acceptable salt of a polysulphated low molecular weight heparin is enoxaparin sodium.

Antibodies can include generally globular plasma proteins (~150 kDa) that are also known as immunoglobulins which share a basic structure. As they can have sugar chains added to amino acid residues, they may also be classified as glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that can include four polypeptide chains; two heavy chains and two light chains connected by disulfide bonds between cysteine residues. Each heavy chain can be about 440 amino acids long; each light chain can be about 220 amino acids long. Heavy and light chains may each contain intra-chain disulfide bonds which stabilize their folding. Each chain is composed of structural domains called Ig domains. These domains typically contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains p and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of antibodies can be similar, the unique property of a given antibody is determined by the variable (V) regions, as detailed above. More specifically, variable loops, often three on the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is usually the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their inter-chain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H inter-chain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion. Pharmaceutically acceptable solvates are for example hydrates.

In some embodiments, medicaments of various viscosities can be injected. For example, viscosity could range from about 3 to about 50 cP. In other embodiments, viscosity could be less than about 3 cP or greater than about 50 cP. Injection can further include delivering a medicament to a sub-cutaneous, an intra-muscular, or a transdermal location within a patient's body. The medicament can be in the form of a liquid, gel, slurry, suspension, particle, powder, or other type.

Typical injection volumes can range from about 1 mL to about 10 mL. Rates of injection may be about 0.5 mL/min, about 0.2 mL/min, or about 0.1 mL/min. Such injection profiles may be generally constant in flow rate, generally continuous in duration, or both generally constant and generally continuous. These injections can also occur in a single step of administration. Such injection profiles may be referred to as bolus injections.

Delivery devices functioning with such medicaments may utilize a needle, cannula, or other injection element configured to deliver a medicament to the patient. Such an injection element may, for example, have an external size or diameter of 27 G or less. Further, the injection element could be rigid, flexible, and formed using a range of one or more materials. And in some embodiments, the injection element may include two or more components. For example, a rigid trocar may operate in conjunction with a flexible cannula. Initially, both the trocar and cannula may move together to pierce the skin. The trocar may then retract while the cannula remains at least partially within the target tissue. Later, the cannula may separately retract into the delivery device.

An insertion mechanism for inserting the needle may take any suitable form. It may be a mechanical spring based mechanism. Alternatively, the insertion mechanism may for instance include an electric motor and a gear mechanism that causes insertion of the insertion element into the user. Alternatively, the insertion mechanism may be a gas or fluid pressure operated mechanism, in which case the needle driving energy source is either a reservoir of pressurized gas or a chemical system in which two or more chemicals are mixed together to produce gas or fluid pressure.

It will be appreciated that the inventive concept of packaging for medicament delivery devices may be applicable to LVDs. However, the invention is not intended to be limited to this particular type of medicament delivery device and is intended to cover alternative types of medicament delivery devices which include a medicament container to be received in a medicament delivery device which may include, but are not limited to, patch pumps and infusion pumps.

The invention claimed is:

1. A packaging for a medical device and medicament, the packaging comprising:
    a packaging body having a first region and a second region, the packaging body including a hinge between the first and second regions such that the first and second regions are pivotable about the hinge from a storage position in which the first and second regions are spaced apart to a loading position in which the first region lies adjacent the second region; and
    a medicament delivery device comprising a delivery mechanism for administering medicament to a patient;
    wherein the medicament delivery device is received in the first region and a medicament container received in the second region, the medicament delivery device including a chamber configured to receive the medicament container, the chamber and medicament container being equidistantly spaced from the hinge and arranged such that the medicament container is loaded into the chamber when the first and second regions are pivoted into the loading position.

2. The packaging according to claim 1, wherein the first and second regions each comprise a recess in the packaging body.

3. The packaging according to claim 1, wherein the medicament delivery device includes a needle through which medicament is received from the medicament container in use, and the medicament container comprises a pierceable region to be pierced by the needle of the medicament delivery device.

4. The packaging according to claim 3, wherein the medicament delivery device is configured to automatically pierce the pierceable region of the medicament container when the first and second regions of the packaging body are pivoted into the loading position and the medicament container is loaded into the chamber.

5. The packaging according to claim 3, wherein the medicament container comprises a cartridge and the pierceable region comprises a seal over an opening in the cartridge.

6. The packaging according to claim 1, wherein the medicament container is adhered to the second region of the packaging body by a non-permanent adhesive.

7. The packaging according to claim 6, wherein the medicament delivery device includes a holding mechanism for retaining the medicament container within the chamber and a force required to remove the medicament container from the holding mechanism is greater than a force with which the non-permanent adhesive secures the medicament container to the second region of the packaging body.

8. The packaging according to claim 1, further comprising a cover secured to the packaging body and covering the first and second regions to define a sealed interior space within the packaging.

9. The packaging according to claim 8, wherein the sealed interior space comprises an inert atmosphere.

10. The packaging according to claim 8, wherein the sealed interior space comprises at least a partial vacuum.

11. The packaging according to claim 1, further comprising:
    a first cover secured to the packaging body and covering the first region to define a first sealed interior space within the packaging, and
    a second cover secured to the packaging body and covering the second region to define a second sealed interior space within the packaging.

12. The packaging according to claim 11, wherein each of the first and second sealed interior spaces comprises an inert atmosphere.

13. The packaging according to claim 11, wherein each of the first and second sealed interior spaces comprises at least a partial vacuum.

14. The packaging according to claim 1, wherein the packaging body is a unitary component and the hinge is a living hinge formed integrally with the packaging body.

15. The packaging according to claim 1, wherein the first and second regions of the body comprise separate components connected by the hinge.

16. The packaging according to claim 15, wherein the hinge comprises a flexible strip of material connecting the first and second regions of the body.

17. The packaging according to claim 1, wherein the medicament container contains a medicament.

18. The packaging according to claim 1, wherein the medicament delivery device comprises a cooperating element arranged to cooperate with the medicament container to allow medicament transfer from the medicament container to the medicament delivery device when the medicament container is loaded into the chamber.

19. A method comprising:
    pivoting a first region and a second region of a packaging body relative to one another about a hinge of the packaging body from a storage position in which the first and second regions are spaced apart to a loading position in which the first region lies adjacent to the second region; and
    causing a medicament container in the second region to be loaded into a chamber of a medicament delivery device in the first region by the first and second regions being pivoted into the loading position, the medicament delivery device comprising a delivery mechanism for administering medicament to a patient.

20. The method of claim 19, wherein causing the medicament container to be loaded into the chamber comprises inserting the medicament container into the chamber while pivoting the first and second regions to the loading position, thereby engaging the medicament container to a holding mechanism in the chamber such that the medicament container remains coupled with the chamber when the first and second regions are pivoted away from the loading position.

21. The method of claim 19, further comprising removing a cover inhibiting the first and second regions from pivoting into the loading position while the cover is engaged with the packaging body.

22. The method of claim 19, wherein a seal of the medicament container is pierced by a needle within the chamber when the first and second regions are in the loading position, thereby transferring medicament to a medicament delivery device.

* * * * *